United States Patent [19]

Meek et al.

[11] Plant 4,764

[45] Sep. 8, 1981

[54] CHRYSANTHEMUM PLANT

[75] Inventors: Jack M. Meek; William E. Duffett, both of Salinas, Calif.

[73] Assignee: Yoder Brothers, Inc., Barberton, Ohio

[21] Appl. No.: 160,825

[22] Filed: Jun. 18, 1980

[51] Int. Cl.[3] ..... A01H 5/00

[52] U.S. Cl. ..... Plt./74

[58] Field of Search ..... Plt./74

*Primary Examiner*—James R. Feyrer

*Attorney, Agent, or Firm*—Schwartz, Jeffery, Schwaab, Mack, Blumenthal & Koch

[57] ABSTRACT

A chrysanthemum plant known by the cultivar name Pert having flat capitulum form; daisy capitulum type; dark yellow ray floret color; diameter across face of capitulum ranging from 70 to 90 mm. at maturity; uniform eight week photoperiodic flowering response to short days; short plant height when grown as a pinched spray pot, and semi-spreading branching pattern.

3 Drawing Figures

The present invention comprises a new and distinct cultivar of *Chrysanthemum morifolium,* Ramat., hereinafter referred to by the cultivar name Pert.

Pert is a product of a planned breeding program which had the objective of creating new chrysanthemum cultivars with daisy capitulum type, with yellow ray floret color, with eight week flowering response, and with the ability to produce commercially acceptable quality in year round pot mum programs. Such traits in combination were not present in previously available commercial cultivars.

Pert was originated from a cross made in a controlled breeding program in Barberton, Ohio in 1977. The female parent was an unnamed yellow daisy seedling (#76025030) originated from a hybridization of #75026002 (unnamed seedling) and Dixie, disclosed in U.S. Plant Pat. No. 3,655. The male parent of Pert was an unnamed yellow daisy seedling (#70363069) originated from a hybridization of Dramatic, disclosed in U.S. Plant Pat. No. 3,189, and Bonnie Jean (unpatented; commercially available).

Pert was discovered and selected as one flowering plant within the progeny of the stated parentage by William E. Duffett on Aug. 10, 1978 in a controlled environment in Salinas, Calif.

The first act of asexual reproduction of Pert was accomplished when vegatative cuttings were taken from the initial selection in November, 1978 in a controlled environment in Salinas, Calif. by a technician working under formulations established and supervised by Jack M. Meek. Continued asexual reproduction by vegetative cuttings for evaluative tests in flowering and stock programs in conjunction with horticultural examination of selected units initiated Feb. 21, 1979 has demonstrated that the combination of characteristics as herein disclosed for Pert is firmly fixed and retained through successive generations of asexual reproduction.

Pert has not been observed under all possible environmental conditions. The phenotype may vary significantly with variations in environment such as temperature, light intensity and daylength. The following observations, measurements, and comparisons describe plants grown in Salinas, Calif., under greenhouse conditions which approximate those generally used in commercial practice.

The following traits have been repeatedly observed and are determined to be basic characteristics of Pert which in combination distinguish this chrysanthemum as a new and distinct cultivar:

(1) flat capitulum form;

(2) daisy capitulum type;

(3) dark yellow ray floret color;

(4) yellow-green (immature) to yellow (mature) disc floret color;

(5) diameter across face of capitulum ranging from 70 to 90 mm. at maturity;

(6) uniform eight week photoperiodic flowering response to short days;

(7) short plant height (requiring 2–3 long day weeks prior to pinch and short days, and one application 2500 ppm B-9 SP 14 to 21 days after the beginning of short days to attain a flowered plant height of 30 to 45 cm.); and (8) semi-spreading branching pattern.

The accompanying photographic drawings show typical inflorescence and foliage characteristics of Pert, with the colors being as nearly true as possible with illustrations of this type. Sheet 1 is a color photograph of a flowering plant of Pert. Sheet 2 is a black and white photograph showing three views of the inflorescence of Pert. Sheet 3 is a black and white photograph showing the foliage of Pert at three stages of growth.

Of the many commercial cultivars known to the present inventors, the most similar in comparison to Pert is Ritz, disclosed in U.S. Plant Pat. No. 3,868. Reference is made to attached Chart A which compares certain characteristics of Pert to those same characteristics of Ritz. In general comparison to Ritz, Pert has more spreading branching pattern, larger diameter across face of capitulum, and shorter flowering response period. The ray floret color, capitulum form, capitulum type, and plant height of Pert are similar to those same characteristics of Ritz.

In the following description color references are made to A Limit Color Cascade by the Munsell Company, 1972 edition. The color values were determined between 7:30 and 8:00 a.m. on Mar. 28, 1980 under 100 foot-candle light intensity at Salinas, Calif.

Classification:

*Botanical.*—*Chrysanthemum morifolium,* Ramat., cv Pert.

*Commerical.*—Pinched daisy spray pot.

I. INFLORESCENCE (See sheets 1 and 2)

A. Capitulum:
*Form.*—Flat.
*Type.*—Daisy.
*Diameter across face.*—70 to 90 mm.

B. Corolla of ray florets:
*General tonality from a distance of* 3 *meters.*—27-4 to 27-3.
*Color* (*abaxial*).—25-6 to 25-5.
*Color* (*adaxial*).—25-5 to 25-4.

C. Corolla of disc florets:
*Color* (*mature*).—Approximately 28-5.
*Color* (*immature*).—Approximately 23-10.

D. Reproductive organs:
*Androecium.*—Present disc florets only; scant to few; scant pollen.
*Gynoecium.*—Present both ray and disc florets.

II. PLANT

A. General appearance:
*Height.*—Short.
*Branching pattern.*—Semi-spreading.

B. Foliage (See sheet 3):
*Color* (*abaxial*).—Approximately 20-15.
*Color* (*adaxial*).—Approximately 20-15 overlaid with white.
*Shape.*—Moderately lobed and slightly serrated.

CHART A

COMPARISON OF PERT AND RITZ

| CULTIVAR | RAY FLORET COLOR | CAPITULUM FORM AND TYPE | BRANCHING PATTERN |
|---|---|---|---|
| Pert | Dark Yellow | flat daisy | semi-spreading |
| Ritz | Dark Yellow | flat daisy | semi-upright |

| CULTIVAR | DIAMETER ACROSS FACE OF CAPITULUM | PLANT HEIGHT | FLOWERING RESPONSE PERIOD |
|---|---|---|---|
| Pert | 70 to 90 mm. | short | 8 week |
| Ritz | 65 to 75 mm. | short | 9 week |

COMPARISONS MADE OF PLANTS GROWN AS PINCHED SPRAY POTS IN SALINAS, CALIFORNIA.

We claim:

1. A new and distinct cultivar of *Chrysanthemum morifolium,* Ramat., plant known by the cultivar name Pert, as described and illustrated, and particularly characterized as to uniqueness by the combined characteristics of flat capitulum form; daisy capitulum type; dark yellow ray floret color; diameter across face of capitulum ranging from 70 to 90 mm. at maturity; uniform eight week photoperiodic flowering response to short days; short plant height when grown as a pinched spray pot, and semi-spreading branching pattern.

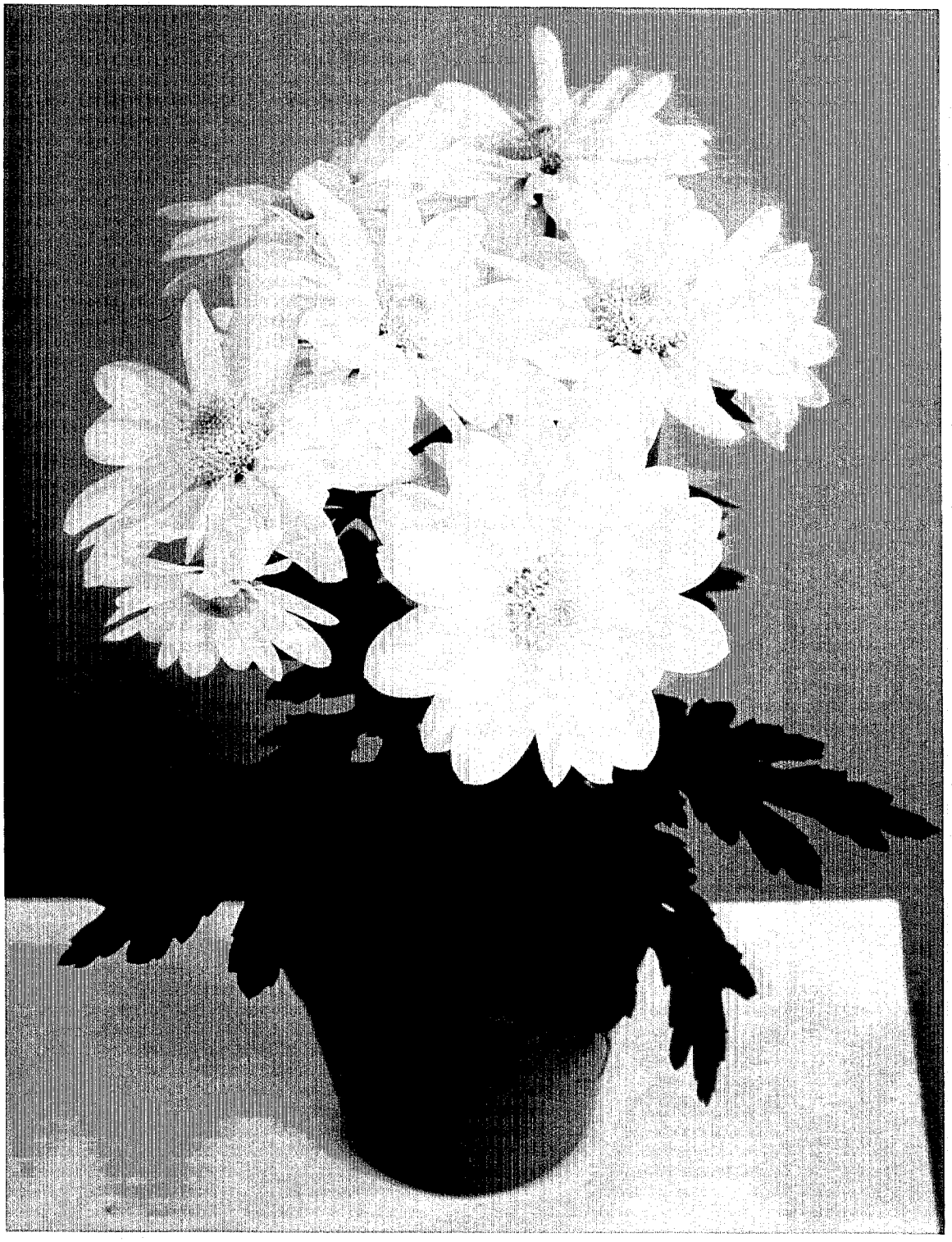

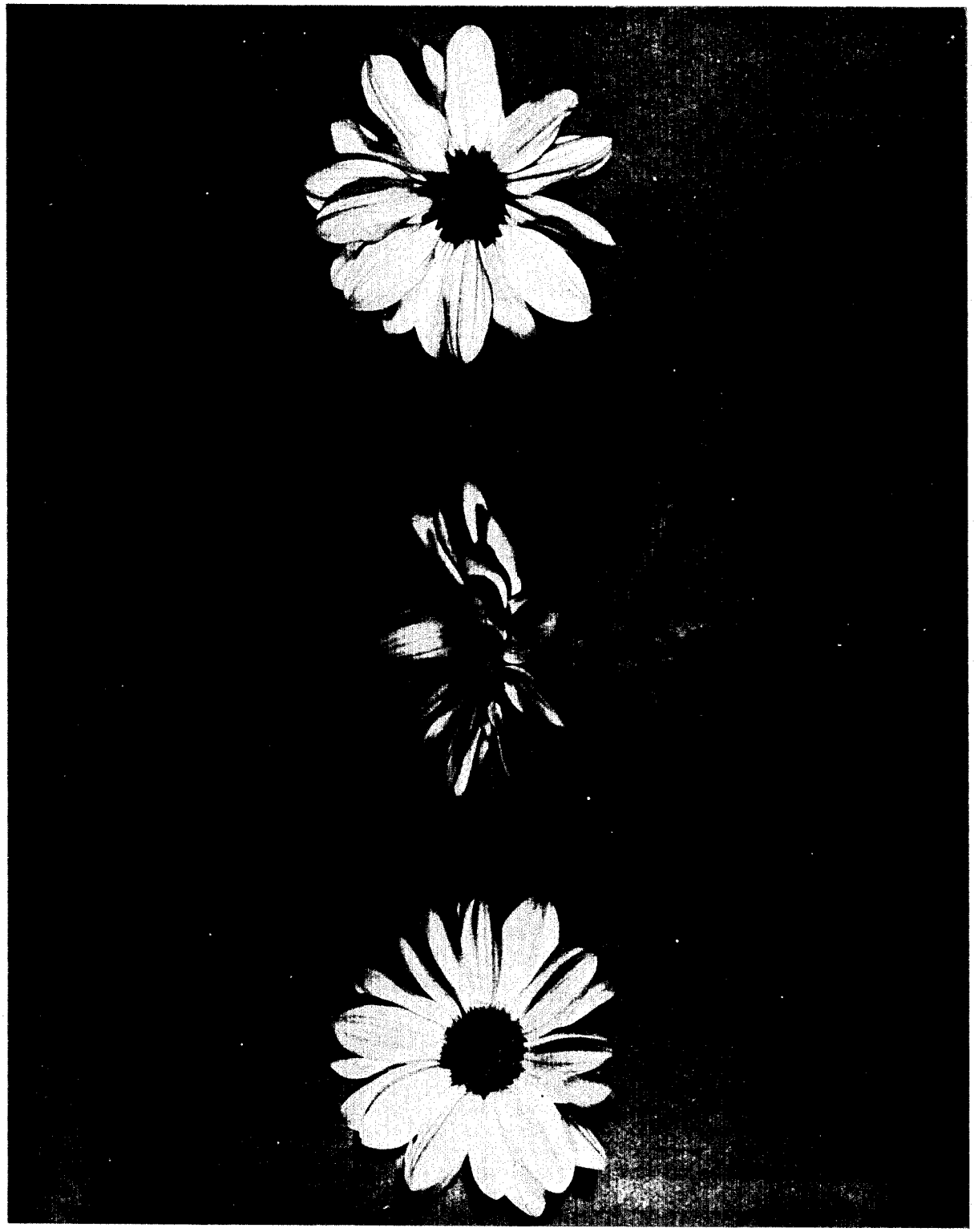

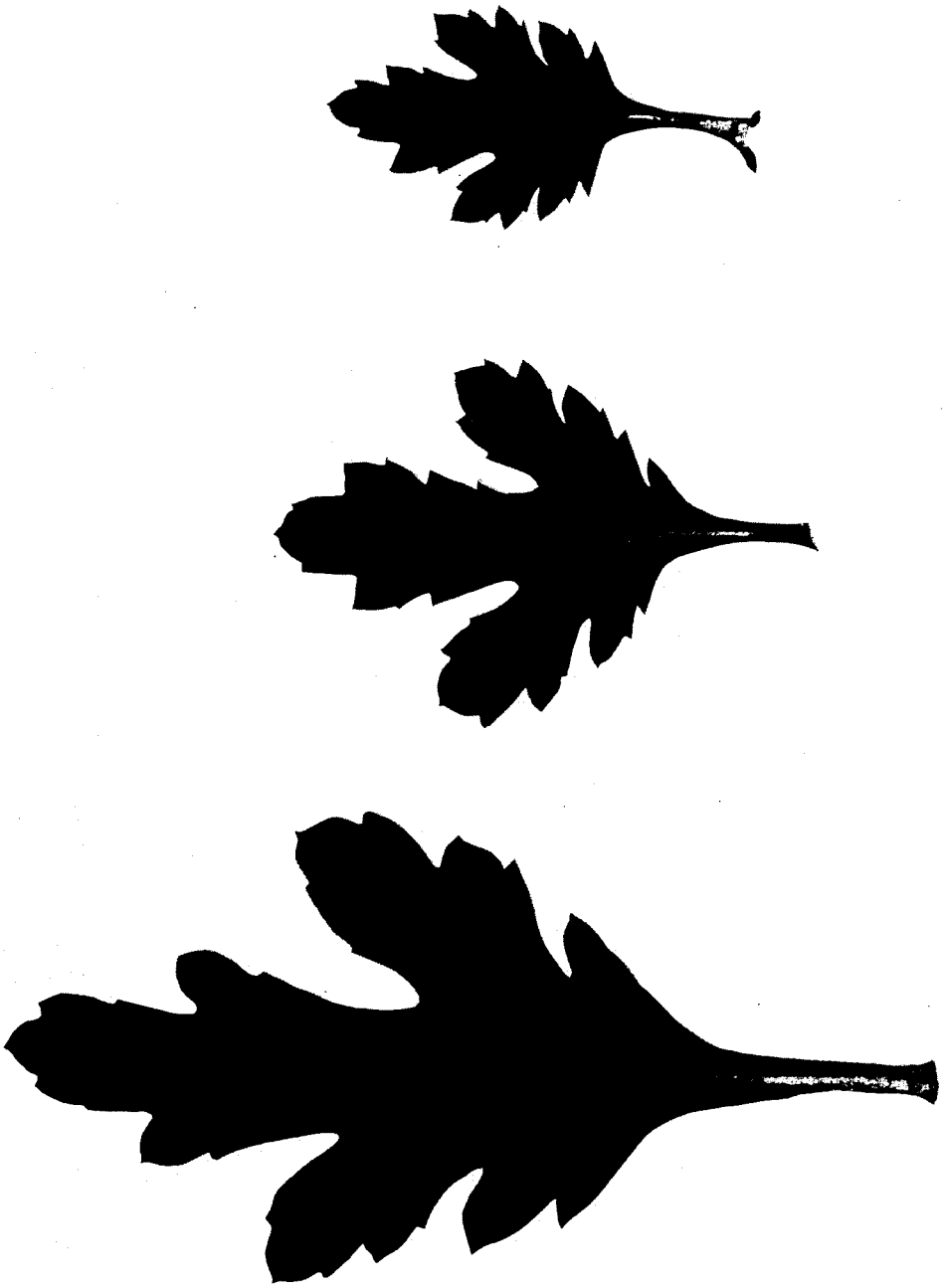

* * * * *